(12) United States Patent
James et al.

(10) Patent No.: US 10,351,897 B2
(45) Date of Patent: Jul. 16, 2019

(54) ACETAMINOPHEN ADDUCTS AND METHODS OF USE THEREOF

(71) Applicants: BioVentures, LLC, Little Rock, AR (US); Arkansas Children's Hospital Research Institute, Little Rock, AR (US)

(72) Inventors: Laura P. James, Little Rock, AR (US); Jack Hinson, Little Rock, AR (US); Dean Roberts, Little Rock, AR (US); Pritmohinder S. Gill, Little Rock, AR (US)

(73) Assignee: BioVentures, LLC, Little Rock, AR (US)

( * ) Notice: Subject to any disclaimer, the term of this patent is extended or adjusted under 35 U.S.C. 154(b) by 0 days.

(21) Appl. No.: 15/118,297

(22) PCT Filed: Feb. 13, 2015

(86) PCT No.: PCT/US2015/015905
§ 371 (c)(1),
(2) Date: Aug. 11, 2016

(87) PCT Pub. No.: WO2015/123574
PCT Pub. Date: Aug. 20, 2015

(65) Prior Publication Data
US 2017/0175166 A1    Jun. 22, 2017

Related U.S. Application Data

(60) Provisional application No. 61/940,023, filed on Feb. 14, 2014.

(51) Int. Cl.
| | | |
|---|---|---|
| *G01N 33/53* | (2006.01) | |
| *C12Q 1/48* | (2006.01) | |
| *C07K 14/47* | (2006.01) | |
| *C12N 9/10* | (2006.01) | |
| *C12Q 1/527* | (2006.01) | |

(52) U.S. Cl.
CPC ............ *C12Q 1/48* (2013.01); *C07K 14/4708* (2013.01); *C12N 9/1007* (2013.01); *C12N 9/107* (2013.01); *C12N 9/1014* (2013.01); *C12N 9/1096* (2013.01); *C12Q 1/527* (2013.01); *C12Y 201/01005* (2013.01); *G01N 33/53* (2013.01)

(58) Field of Classification Search
CPC .. C07K 14/4708; C12N 9/1014; C12N 9/107; C12N 9/1096; C12N 9/1007; C12Q 1/48; C12Q 1/527; G01N 33/53; C12Y 201/01005
See application file for complete search history.

(56) References Cited

U.S. PATENT DOCUMENTS

| 5,103,021 A | 4/1992 | Pyare |
|---|---|---|
| 5,620,890 A | 4/1997 | Kamps-Holtzapple et al. |
| 5,747,352 A | 5/1998 | Yon et al. |
| 6,054,303 A | 4/2000 | Davalian et al. |
| 6,352,862 B1 | 3/2002 | Davis et al. |
| 7,700,740 B2 | 4/2010 | Garvia-Martinez et al. |
| 2004/0185040 A1 | 9/2004 | Garcia-Martinez et al. |
| 2005/0136552 A1 | 6/2005 | Buechler |
| 2009/0263839 A1* | 10/2009 | James ............... G01N 33/54386 435/7.93 |
| 2011/0004955 A1 | 1/2011 | Abad et al. |
| 2011/0214205 A1 | 9/2011 | Dietrich et al. |
| 2012/0171699 A1 | 7/2012 | Goodman et al. |
| 2012/0246748 A1 | 9/2012 | Guo et al. |
| 2012/0301897 A1 | 11/2012 | James et al. |
| 2012/0322073 A1 | 12/2012 | Lopez-Girona et al. |
| 2013/0029322 A1 | 1/2013 | Jansen-Durr et al. |
| 2013/0287783 A1 | 10/2013 | Frank et al. |
| 2013/0333061 A1 | 12/2013 | Wu et al. |

FOREIGN PATENT DOCUMENTS

| EP | 0095229 A2 | 11/1983 |
|---|---|---|
| WO | 198808534 A1 | 11/1988 |
| WO | 2009131998 A1 | 10/2009 |
| WO | 2015123574 A1 | 8/2015 |
| WO | 2016090163 A2 | 6/2016 |
| WO | 2016090163 A3 | 6/2016 |

OTHER PUBLICATIONS

Devern et al. Measurement of serum acetaminophen-protein adducts in patients with acute liver failure Gastroenterology 2006, vol. 130, pp. 687-694. (Year: 2006).*
Davern et al. Measurement of serum acetaminophen-protein adducts in patiens with acute liver failure. Gastroenterology, 2006, vol. 130, pp. 687-694. (Year: 2006).*
Extended European Search Report dated Oct. 25, 2017 from related European Patent Application No. 15748750.5; 8 pgs.
Bartolone, J. et al., "Immunochemical Detection of Acetaminophen-Bound Liver Proteins," Biochem. Pharmacol., 1987, pp. 1193-1196, vol. 36, No. 8.

(Continued)

*Primary Examiner* — Shafiqul Haq
(74) *Attorney, Agent, or Firm* — Polsinelli PC

(57) ABSTRACT

The present disclosure relates to acetaminophen protein adducts and methods of diagnosing acetaminophen toxicity using the acetaminophen protein adducts. The present disclosure provides acetaminophen (APAP)-protein adducts and methods of detecting acetaminophen-induced toxicity in a subject using APAP-protein adducts. One aspect of the present disclosure provides an APAP-protein adduct for diagnosing acetaminophen-induced toxicity. According to the present disclosure, the inventors have identified proteins that are modified by N-acetyl-pbenzoquinoneimine (NAPQI) in subjects with acetaminophen-induced toxicity. Non-limiting examples of proteins modified by NAPQI include betaine-homocysteine S-methyltransferase 1, cytoplasmic aspartate aminotransferase, 1,4-alpha-glucan branching enzyme, formimidoyltransferase-cyclodeaminase, and dystrophin.

6 Claims, No Drawings

(56) References Cited

OTHER PUBLICATIONS

Bartolone, J. et al., "Immunochemical Analysis of Acetaminophen Covalent Binding to Proteins, Partial Characterization of the Major Acetaminophen-Binding Liver Proteins. Partial Characterization of the Major Acetaminophen-Binding Liver Proteins," Biochem. Pharmacol., 1988, pp. 4763-4774, vol. 37, No. 24, Pergamon Press plc, Great Britain.

Betowski, L. et al., "Direct Analysis of Rat Bile for Acetaminophen and Two of its Conjugated Metabolites via Thermospray Liquid Chromatography/Mass Spectrometry," Biomedical and Environmental Mass Spectrometry, 1987, pp. 705-709, vol. 14, No. 12.

Chaudhuri, S. et al., "Acetaminophen hepatotoxicity and HIF-1α induction in mice occurs without hypoxia," Toxicol. Appl. Pharmacol., May 1, 2011, pp. 211-220, vol. 252, No. 3.

Coles, B. et al., "The Spontaneous and Enzymatic Reaction of N-Acetyl-p-benzoquinonimine with Glutathione: A Stopped-Flow Kinetic Study," Archives of Biochemistry and Biophysics, Jul. 1988, pp. 253-260, vol. 264, No. 1.

Extended European Search Report dated May 6, 2011 from related European Patent Application No. 097353431; 9 pgs.

Ferguson, D. et al., "Acetaminophen-Induced Alterations in Pancreatic β Cells and Serum Insulin Concentrations in B6C3F1 Mice," Toxicology and Applied Pharmacology, 1990, pp. 225-243, vol. 104, No. 2.

Fountoulakis, M. et al., "Two-dimensional database of mouse liver proteins: Changes in hepatic protein levels following treatment with acetaminophen or its nontoxic regioisomer 3-acetamidophenol," Electrophoresis, 2000, pp. 2148-2161, vol. 21, Wiley-VCH Verlag GmbH, Weinheim.

Getek, T. et al., "Utility of Solution Electrochemistry Mass Spectrometry for Investigating the Formation and Detection of Biologically Important Conjugates of Acetaminophen," Journal of Chromatography, 1989, pp. 245-256, vol. 474, No. 1.

Gibson, J. et al., "Mechanism of Acetaminophen-Induced Hepatotoxicity: Covalent Binding versus Oxidative Stress," Chem. Res. Toxicol., 1996, pp. 58-585, vol. 9, No. 3.

Gillette, J. et al., "Formation of Chemically Reactive Metabolites of Phenacetin and Acetaminophen," Biological Reactive Intermediates—II, Chemical Mechanisms and Biological Effects Part B, Adv. Exp. Med. Biol., 1981, pp. 931-950, vol. 136.

Halmes, N. et al., "Glutamate Dehydrogenase Covalently Binds to a Reactive Metabolite of Acetaminophen," Chem. Res. Toxicol., 1996, pp. 541-546, vol. 9, No. 2.

Halmes, N. et al., "The acetaminophen regioisomer 3'-hydroxyacetanilide inhibits and covalently binds to cytochrome P450 2E1," Toxicology Letters, 1998, pp. 65-71, vol. 94, No. 1.

Heard, K. et al., "Acetaminophen-cysteine adducts during therapeutic dosing and following overdose," BMC Gastroenterology, 2011, pp. 1-9, vol. 11, No. 20.

Hu, Z. et al., "Quantitative Liver-Specific Protein Fingerprint in Blood: A Signature for Hepatotoxicity," Theranostics, 2014, pp. 215-228, vol. 4, No. 2, Ivyspring International Publisher.

Hinson, J. et al., "Acetaminophen-induced hepatotoxicity," Life Sciences, Jul. 13, 1981, pp. 107-116, vol. 29, No. 2 (abstract only).

Hinson, J. et al., "Phase II enzymes and bioactivation," Can. J. Physiol. Pharmacol., 1995, pp. 1407-1413, vol. 73, No. 10, Printed in Canada.

Hinson, J. et al., "3-(Glutathion-S-yl)acetaminophen: A Biliary Metabolite of Acetaminophen," Drug Metabolism and Disposition, 1982, pp. 47-50, vol. 10, No. 1.

Hinson, J. et al., "3-Hydroxyacetaminophen: A Microsomal Metabolite of Acetaminophen: Evidence Against an Epoxide as the Reactive Metabolite of Acetaminophen," Drug Metabolism and Disposition, 1980, pp. 289-294, vol. 8, No. 5.

Hinson, J. et al., "A Simple High-Pressure Liquid Chromatographic Assay for the N-Hydroxy Derivatives of Phenacetin, Acetaminophen, 2-Acetylaminofluorene, and Other Hydroxamic Acids," Analytical Biochemistry, 1980, pp. 462-467, vol. 101.

Hinson, J. et al., "Acetaminophen-Induced Alterations in Blood Glucose and Blood Insulin Levels in Mice," Research Communications in Chemical Pathology and Pharmacology, Mar. 1984, vol. 43, No. 3.

Hinson, J. et al., "Acetaminophen-Induced Hepatic Glycogen Depletion and Hyperglycemia in Mice," Biochemical Pharmacology, 1983, pp. 1979-1988, vol. 32, No. 13, Pergamon Press Ltd, Great Britain.

Hinson, J. et al., "Immunochemical Detection of Drug-Protein Adducts in Acetaminophen Hepatotoxicity," Adv. Exp. Med. Biol., 1996, pp. 47-55, vol. 387.

Hinson, J. et al., "Kinetic Evidence of Multiple Chemically Reactive Intermediates in the Breakdown of Phenacetin N-O-Glucuronide," Pharmacology, 1979, pp. 237-248, vol. 19.

Hinson, J. et al., "Mechanism of paracetamol toxicity," The Lancet, Mar. 24, 1990, p. 732, vol. 335, No. 8691.

Hinson, J. et al., "Mechanisms of Acetaminophen Toxicity: Immunochemical Detection of Drug-Protein Adducts," Drug Metabolism Reviews, 1995, pp. 73-92, vol. 27, Nos. 1 & 2.

Hinson, J. et al., "Mechanisms of Acetaminophen-Induced Liver Necrosis," Handb. Exp. Pharmacol., 2010, pp. 369-405, vol. 196 (author manuscript only).

Hinson, J. et al., "Metabolism of [p-18O]-Phenacetin: The Mechanism of Activation of Phenacetin to Reactive Metabolites in Hamsters," Molecular Pharmacology, 1979, pp. 419-427, vol. 15.

Hinson, J. et al., "N-Hydroxyacetaminophen: A Microsomal Metabolite of N-Hydroxyphenacetin But Apparently Not of Acetaminophen," Life Sciences, 1979, pp. 2133-2138, vol. 24.

Hinson, J. et al., "Nitrotyrosine-Protein Adducts in Hepatic Centrilobular Areas following Toxic Doses of Acetaminophen in Mice," Chem. Res. Toxicol., 1998, pp. 604-607, vol. 11, No. 6.

Hinson, J. et al., "Studies on the Microsomal Formation of Arylating Metabolites of Acetaminophen and Phenacetin," Molecular Pharmacology, 1977, pp. 625-633, vol. 13.

Hinson, J. et al., "Western Blot Analysis for Nitrotyrosine Protein Adducts in Livers of Saline-Treated and Acetaminophen-Treated Mice," Toxicological Sciences, 2000, pp. 467-473, vol. 53, No. 2.

Hinson, J., "Reactive Metabolites of Phenacetin and Acetaminophen: A Review," Environmental Health Perspectives, 1983, pp. 71-79, vol. 49.

International Search Report and Written Opinion dated Jun. 19, 2009 from related PCT Patent Application No. PCT/US2009/041247; 10 pgs.

International Search Report and Written Opinion dated May 18, 2015 from related PCT Patent Application No. PCT/US2015/015905; 8 pgs.

International Search Report and Written Opinion dated Feb. 25, 2016 from related PCT Patent Application No. PCT/US2015/063786; 15 pgs.

James, L. et al., "Acetaminophen-Associated Hepatic Injury: Evaluation of Acetaminophen Protein Adducts in Children and Adolescents With Acetaminophen Overdose," NIH Public Access Author Manuscript, 17 pgs., Clin. Pharmacol. Ther., Dec. 2008, pp. 684-690, vol. 84, No. 6.

James, L. et al., "Correlation of MCP1 with Toxicity of Acetaminophen Overdose," Journal of the University of Arkansas for Medical Sciences, Jun. 2004, pp. 424-425, vol. 100, No. 12.

James, L. et al., "Effect of N-Acetylcysteine on Acetaminophen Toxicity in Mice: Relationship to Reactive Nitrogen and Cytokine Formation," Toxicological Sciences, 2003, pp. 458-467, vol. 75.

James, L. et al., "Evaluation of Occult Acetaminophen Hepatotoxicity in Hospitalized Children Receiving Acetaminophen," Clin. Pediatr, 2001, pp. 243-248, vol. 40.

James, L. et al., "Pharmacokinetics of Acetaminophen-Protein Adducts in Adults with Acetaminophen Overdose and Acute Liver Failure," Drug Metabolism and Disposition, 2009, pp. 1779-1784, vol. 37, No. 8.

Keller, R. et al., "Mechanism of Acetaminophen-Stimulated NADPH Oxidation Catalyzed by the Peroxidase-H2O2 System," Drug Metabolism and Disposition, 1991, pp. 184-187, vol. 19, No. 1.

(56) References Cited

OTHER PUBLICATIONS

Matthews, A. et al., "Acetaminophen-Induced Hepatotoxicity, Analysis of Total Covalent Binding Vs. Specific Binding to Cysteine," Drug Metabolism and Disposition, 1996, pp. 1992-1196, vol. 24, No. 11.

Matthews, A. et al., "Comparison of covalent binding of acetaminophen and the regioisomer 3'-hydroxyacetanilide to mouse liver protein," Toxicology Letters, 1997, pp. 77-82, vol. 90.

Merrick, B. et al., "Alterations in the Rat Serum Proteome during Liver Injury from Acetaminophen Exposure," JPET, 2006, pp. 792-802, vol. 318, No. 2, USA.

Extended European Search Report dated May 16, 2018 from related European Patent Application No. 15865732.0; 9 pgs.

James, L. et al., "Acetaminophen-Induced Hepatotoxicity," Drug. Metab. Dis., 2003, pp. 1499-1506, vol. 31, No. 12, The American Society for Pharmacology and Experimental Therapeutics, USA.

Partial Supplementary European Search Report dated Jul. 19, 2017 from related European Patent Application No. 15748750.5; 11 pgs.

Qiu, Y. et al., "Identification of the Hepatic Protein Targets of Reactive Metabolites of Acetaminophen in Vivo in Mice Using Two-dimensional Gel Electrophoresis and Mass Spectrometry," J. Biol. Chem., Jul. 10, 1998, pp. 17940-17953, vol. 273, No. 28, The American Society for Biochemistry and Molecular Biology, Inc.

Chothia, C. et al., "Canonical Structures for the Hypervariable Regions of Immunoglobulins," J. Mol. Biol., 1987, pp. 901-917, vol. 196, Academic Press Limited.

Chothia, C. et al., "Conformations of immunoglobulin hypervariable regions," Nature, Dec. 1989, pp. 878-883, vol. 342, Nature Publishing Group.

Office Action dated Aug. 24, 2018 from related European Patent Application No. 15748750.5; 4 pgs.

Office Action dated Oct. 23, 2018 from related Japanese Patent Application No. 2016-569567; 4 pgs.

Office Action dated Sep. 30, 2011 from related U.S. Appl. No. 12/427,434; 8 pgs.

Office Action dated Sep. 10, 2012 from related European Patent Application No. 09735343.7; 6 pgs.

Pang, K. et al., "High-Performance Liquid Chromatographic Assay for Acetaminophen and Phenacetin in the Presence of Their Metabolites in Biological Fluids," J. Chromatography, 1979, pp. 165-175, vol. 174.

Peters, T., "Serum Albumin: Recent Progress in the Understanding of Its Structure and Biosynthesis," Clin. Chem., 1977, pp. 5-12, vol. 23, No. 1.

Potter, D. et al., "Epitope Characterization of Acetaminophen Bound to Protein and Nonprotein Sulfhydryl Groups by an Enzyme-Linked Immunosorbent Assay," JPET, 1989, pp. 182-189, vol. 248, No. 1.

Potter, D. et al., "Acetaminophen Peroxidation Reactions," Drug Metabolism Reviews, 1989, pp. 341-358, vol. 20, Nos. 2-4.

Potter, D. et al., "Horseradish Peroxidase-Catalyzed Oxidation of Acetaminophen to Intermediates that Form Polymers or Conjugate with Glutathione," Molecular Pharmacology, 1986, pp. 155-162, vol. 29, No. 2.

Potter, D. et al., "Identification of Acetaminophen Polymerization Products Catalyzed by Horseradish Peroxidase," J. Biol. Chem., Oct. 5, 1985, pp. 12174-12180, vol. 260, No. 22.

Potter, D. et al., "Mechanisms of Acetaminophen Oxidation to N-Acetyl-P-benzoquinone Imine by Horseradish Peroxidase and Cytochrome P-450," J. Biol. Chem., Jan. 25, 1987, pp. 966-973, vol. 262, No. 3.

Potter, D. et al., "Reactions of Glutathione with Oxidative Intermediates of Acetaminophen," Adv. Exp. Med. Biol., 1986, pp. 763-772, vol. 197.

Potter, D. et al., "Reactions of N-Acetyl-p-benzoquinone Imine with Reduced Glutathione, Acetaminophen, and NADPH," Molecular Pharmacology, 1986, pp. 33-41, vol. 30.

Potter, D. et al., "The 1- and 2-Electron Oxidation of Acetaminophen Catalyzed by Prostaglandin H Synthase," J. Biol. Chem., Jan. 25, 1987, pp. 974-980, vol. 262, No. 3.

Pumford, N. et al., "Immunochemical Quantitation of 3-(Cystein-S-yl)acetaminophen Protein Adducts in Subcellular Liver Fractions Following a Hepatotoxic Dose of Acetaminophen," Biochemical Pharmacology, 1990, pp. 573-579, vol. 40, No. 3, Pergamon Press plc, Great Britain.

Pumford, N. et al., "Immunochemical Quantitation of 3-(Cystein-S-yl)acetaminophen Adducts in Serum and Liver Proteins of Acetaminophen-Treated Mice," JPET, 1989, pp. 190-196, vol. 248, No. 1, The American Society for Pharmacology and Experimental Therapeutics, USA.

Pumford, N. et al., "A Metabolite of Acetaminophen Covalently Binds to the 56 kDa Selenium Binding Protein," Biochemical and Biophysical Research Communications, Feb. 14, 1992, pp. 1348-1355, vol. 182, No. 3.

Pumford, N. et al., "Covalent Binding of Acetaminophen to N-10-Formyl-Tetrahydrofolate Dehydrogenase in Mice," JPET, 1997, pp. 501-505, vol. 280, No. 1.

Pumford, N. et al., "Immunoblot Analysis of Protein Containing 3-(Cystein-S-yl)acetaminophen Adducts in Serum and Subcellular Liver Fractions from Acetaminophen-Treated Mice," Toxicology and Applied Pharmacology, 1990, pp. 001-0012, vol. 104, No. 3.

Roberts, D. et al., "A Sensitive Immunochemical Assay for Acetaminophen-Protein Adducts," JPET, 1987, pp. 527-533, vol. 241, No. 2, The American Society of Pharmacology and Experimental Therapeutics, USA.

Roberts, D. et al., "Critical Considerations in the Immunochemical Detection and Quantitation of Antigenic Biomarkers," Biomedical and Environmental Sciences, 1991, pp. 113-129, vol. 4, Nos. 1-2.

Roberts, D. et al., "Immunohistochemical Localization and Quantification of the 3-(Cystein-S-yl)-acetaminophen Protein Adduct in Acetaminophen Hepatotoxicity," American Journal of Pathology, Feb. 1991, pp. 359-371, vol. 138, No. 2.

Salminen, W. et al., "Immunochemical Comparison of 3'-Hydroxyacetanilide and Acetaminophen Binding in Mouse Liver," Drug Metabolism and Disposition, 1998, pp. 267-271, vol. 26, No. 3.

Schnellmann, J. et al., "Deferoxamine delays the development of the hepatotoxicity of acetaminophen in mice," Toxicology Letters, 1999, pp. 79-88, vol. 106.

Song, W. et al., "One-Step Immunoassay for Acetaminophen and Salicylate in Serum, Plasma, and Whole Blood," J. Analytical Toxicology, Sep. 2003, pp. 366-371, vol. 27.

Webster, P. et al., "Acetaminophen Toxicity in Children: Diagnostic Confirmation Using a Specific Antigenic Biomarker," J. Clin. Pharmacol., 1996, pp. 397-402, vol. 36.

Weeks, B. et al., "Acetaminophen Toxicity to Cultured Rat Embryos," Teratogenesis, Carcinogenesis, and Mutagenesis, 1990, pp. 361-371, vol. 10, No. 5.

Office Action dated May 9, 2019 from related U.S. Appl. No. 15/532,418; 15 pgs.

Rudikoff, S. et al., "Single amino acid substitution altering antigen-binding specificity," PNAS, Mar. 1982, pp. 1979-1983, vol. 79.

* cited by examiner

ACETAMINOPHEN ADDUCTS AND METHODS OF USE THEREOF

CROSS REFERENCE TO RELATED APPLICATIONS

This application claims the benefit of PCT Application PCT/US2015/015905, filed Feb. 13, 2015, which claims the benefit of U.S. provisional application No. 61/940,023, filed Feb. 14, 2014, the disclosures of which are hereby incorporated by reference in its entirety.

GOVERNMENTAL RIGHTS

This invention was made with government support under Grant No. 81406 awarded by the National Institute of Diabetes and Digestive and Kidney Diseases (NIDDK). The government has certain rights in the invention.

FIELD OF THE INVENTION

The present disclosure relates to acetaminophen protein adducts and methods of using the acetaminophen protein adducts to diagnose acetaminophen toxicity.

BACKGROUND OF THE INVENTION

Acetaminophen (APAP) is the most common pharmaceutical product associated with drug toxicity. In severe cases, acetaminophen overdose may lead to acute liver failure (ALF) and death. Over 100,000 telephone calls concerning acetaminophen overdose are made to poison control centers in the U.S. annually. The FDA estimates that approximately 450 deaths are related to acetaminophen overdose annually. For patients that seek treatment within 24 hours of an acetaminophen overdose, and are able to provide accurate information regarding the time and amount of acetaminophen ingested, acetaminophen overdose is relatively straightforward to diagnose and treat. However, current methods of diagnosing acetaminophen overdose, such as the Rumack nomogram, are not very useful to diagnose patients after 24 hours of an acetaminophen overdose, when information regarding time and dose of acetaminophen ingested is not available, or patients that use alcohol, chronically ingest supratherapeutic doses of acetaminophen, or use sustained release acetaminophen formulations. Other laboratory tests, such as serum alanine aminotransferase (ALT) and serum aspartate aminotransferase (AST), indicate the occurrence of liver damage, but neither bioindicator is specific to acetaminophen overdose.

Accordingly, a need exists in the art for a method of accurately diagnosing acetaminophen-induced toxicity, including occult acetaminophen poisoning, even 24 hours or longer after the overdose.

DETAILED DESCRIPTION

The present disclosure provides acetaminophen (APAP)-protein adducts and methods of detecting acetaminophen-induced toxicity in a subject using APAP-protein adducts. Using a method as described herein to detect acetaminophen-induced toxicity may improve patient outcome by identifying subjects who are likely to benefit from appropriate, informed, and timely treatment decisions. Advantageously, such a method may allow the identification of acetaminophen-induced toxicity as the cause of acute liver failure when other methods of identifying acetaminophen-induced toxicity fail in individuals for whom an identifiable etiology cannot be found. A method of the disclosure is also useful in patients with confounding factors where current methods of detecting acetaminophen overdose are not useful, which factors include presentation to the hospital 24 hours after ingesting an acetaminophen overdose, chronic supratherapeutic ingestion of acetaminophen, the abuse of sustained release acetaminophen formulations, or ethanol use.

I. APAP-Protein Adduct

One aspect of the present disclosure provides an APAP-protein adduct for diagnosing acetaminophen-induced toxicity. Acetaminophen-induced toxicity is mediated by conversion of acetaminophen to a reactive metabolite, N-acetyl-p-benzoquinone imine (NAPQI), in the body of a subject. NAPQI covalently binds to cysteine groups in proteins or peptides to form APAP-protein adducts mainly in the liver, and to a lesser degree in other tissues capable of metabolizing acetaminophen. These APAP-protein adducts have the cysteine sulfur group covalently attached to the APAP ring meta to the acetamido group and ortho to the phenol group, and are also called 3-(cystein-S-yl) APAP (3-Cys-A)-protein adducts. NAPQI depletes the liver's natural antioxidant glutathione and directly damages cells in the liver, leading to liver failure and release of APAP-protein adducts into the circulatory system.

According to the present disclosure, the inventors have identified proteins that are modified by NAPQI in subjects with acetaminophen-induced toxicity. Non-limiting examples of proteins modified by NAPQI include betaine-homocysteine S-methyltransferase 1, cytoplasmic aspartate aminotransferase, 1,4-alpha-glucan-branching enzyme, formimidoyltransferase-cyclodeaminase, and dystrophin. A description of each protein that may be modified by NAPQI is given below.

Betaine-homocysteine S-methyltransferase 1 (BHMT): BHMT is a zinc metallo-enzyme that catalyzes the transfer of a methyl group from betaine to homocysteine to produce dimethylglycine and methionine respectively. BHMT belongs to the family of transferases, specifically those transferring one-carbon group methyltransferases. BHMT participates in the metabolism of glycine, serine, threonine and also methionine.

Cytoplasmic aspartate aminotransferase (cAspAT): cAspAT, also known as cytoplasmic cysteine aminotransferase, cytoplasmic cysteine transaminase (cCAT), glutamate oxaloacetate transaminase (GOT), or transaminase A, is a pyridoxal phosphate-dependent enzyme which exists in cytoplasmic (GOT1) and mitochondrial (GOT2) forms. The two enzymes are homodimeric and show close homology. cAspAT plays a role in amino acid metabolism and the urea and tricarboxylic acid cycles.

1,4-alpha-glucan-branching enzyme (GBE1): 1,4-alpha-glucan-branching enzyme, also known as brancher enzyme or glycogen-branching enzyme, is an enzyme that catalyzes the formation of the alpha-1,6-glucosidic linkages in glycogen by scission of a 1,4-alpha-linked oligosaccharide from growing alpha-1,4-glucan chains and the subsequent attachment of the oligosaccharide to the alpha-1,6 position. It takes part in converting glucose to glycogen, adding branches to the growing glycogen molecule.

Formimidoyltransferase-cyclodeaminase (FTCD): FTCD, also known as formiminotransferase-cyclodeaminase, is a folate-dependent enzyme that displays both transferase and deaminase activity. FTCD serves to channel one-carbon units from formiminoglutamate to the folate pool. The enzyme binds and promotes bundling of vimentin filaments originating from the Golgi.

Dystrophin (DMD): Dystrophin is a rod-shaped cytoplasmic protein, and a vital part of a protein complex that connects the cytoskeleton of a muscle fiber to the surrounding extracellular matrix through the cell membrane. This complex is variously known as the costamere or the dystrophin-associated protein complex. Many muscle proteins, such as α-dystrobrevin, syncoilin, synemin, sarcoglycan, dystroglycan and sarcospan, co-localize with dystrophin at the costamere.

As such, an APAP-protein adduct of the disclosure comprises a protein modified with NAPQI, wherein the protein is selected from the group consisting of betaine-homocysteine S-methyltransferase 1, cytoplasmic aspartate aminotransferase, 1,4-alpha-glucan-branching enzyme, formimidoyltransferase-cyclodeaminase, dystrophin, and a combination thereof.

In some embodiments, an APAP-protein adduct of the disclosure comprises betaine-homocysteine S-methyltransferase 1 modified with NAPQI. In specific embodiments, an APAP-protein adduct of the disclosure comprises betaine-homocysteine S-methyltransferase 1 represented by UniProtKB accession number Q93088, modified with NAPQI.

In other embodiments, an APAP-protein adduct comprises cytoplasmic aspartate aminotransferase modified with NAPQI. In specific embodiments, an APAP-protein adduct of the disclosure comprises a cytoplasmic form of cytoplasmic aspartate aminotransferase, modified with NAPQI. In a specific alternative of the embodiments, an APAP-protein adduct of the disclosure comprises cytoplasmic aspartate aminotransferase represented by UniProtKB accession number P17174, modified with NAPQI.

In yet other embodiments, an APAP-protein adduct comprises 1,4-alpha-glucan-branching enzyme modified with NAPQI. In specific embodiments, an APAP-protein adduct of the disclosure comprises 1,4-alpha-glucan-branching enzyme represented by UniProtKB accession number Q04446, modified with NAPQI.

In other embodiments, an APAP-protein adduct comprises formimidoyltransferase-cyclodeaminase modified with NAPQI. In specific embodiments, an APAP-protein adduct of the disclosure comprises formimidoyltransferase-cyclodeaminase represented by UniProtKB accession number O95954, modified with NAPQI.

In additional other embodiments, an APAP-protein adduct comprises dystrophin modified with NAPQI. In specific embodiments, an APAP-protein adduct of the disclosure comprises dystrophin represented by UniProtKB accession number P11532, modified with NAPQI.

As described above, NAPQI covalently binds to cysteine groups in a protein to form APAP-protein adducts. As such, a protein in an APAP-protein adduct of the present disclosure comprises at least one cysteine group modified with NAPQI. Additionally, when a protein in an APAP-protein adduct comprises more than one cysteine residue, one or more than one cysteine residues of the protein may be modified with NAPQI. For instance, 1, 2, 3, 4, 5, 6, 7, 8, 9 or more cysteine residues of the protein may be modified with NAPQI.

An APAP-protein adduct of the present disclosure may comprise a full length protein modified with NAPQI. Alternatively, an APAP-protein adduct may comprise a peptide fragment of a protein, wherein the peptide fragment is modified with NAPQI. An APAP-protein adduct may comprise a peptide fragment of a protein if, for instance, an APAP-protein adduct may be fragmented into peptides in a subject before obtaining a sample for analysis. Additionally, when a sample is obtained and processed for analysis (see below), proteins in the sample may be fragmented as a result of processing the sample for analysis, or may be intentionally fragmented for further analysis. In some embodiments, an APAP-protein adduct comprises a full length protein modified with NAPQI. In other embodiments, an APAP-protein adduct comprises a peptide fragment of a full length protein modified with NAPQI. It should be appreciated by those of skill in the art that in such embodiments, a peptide fragment of a full length protein modified with NAPQI may be of any length, provided that the peptide comprises one or more cysteine residues that are modified with NAPQI.

II. Methods

In other aspects, the disclosure encompasses methods of detecting acetaminophen-induced toxicity in a subject. A method of the disclosure comprises obtaining a biological sample from a subject and processing an amount of the sample, in vitro, to detect one or more APAP-protein adducts, wherein each APAP-protein adduct comprises a protein modified with NAPQI, and wherein the protein is selected from the group consisting of betaine-homocysteine S-methyltransferase 1, cytoplasmic aspartate aminotransferase, 1,4-alpha-glucan-branching enzyme, formimidoyl-transferase-cyclodeaminase, or dystrophin.

(a) Subject

As used herein, the term "subject" refers to a living organism that may be administered acetaminophen. Suitable subjects include, but are not limited to, a human, a livestock animal, a companion animal, a lab animal, and a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In specific embodiments, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In a preferred embodiment, the subject is human. Subjects may be of any age, including newborn, adolescent, adult, middle age, or elderly.

A subject may or may not be having a symptom associated with acetaminophen-induced toxicity. Specifically, the acetaminophen-induced toxicity may be hepatotoxicity. A skilled artisan will appreciate that pathological acetaminophen-induced toxicity likely commences prior to diagnosis or the onset of symptoms associated with acetaminophen-induced toxicity. In some embodiments, a subject is having a symptom associated with acetaminophen-induced toxicity. In other embodiments, a subject is not having a symptom associated with acetaminophen-induced toxicity. In still other embodiments, a subject has detectable acetaminophen-induced toxicity but is not having any other symptom associated with acetaminophen-induced toxicity. In yet still other embodiments, a subject has received acetaminophen. In different embodiments, a subject has received a supratherapeutic dose of acetaminophen. In alternative embodiments, a subject has been suspected of receiving a supratherapeutic dose of acetaminophen. For example, a subject may have liver failure of unclear etiology which may have developed as a result of receiving a supratherapeutic dose of acetaminophen. Early diagnosis of acetaminophen-induced toxicity in the subject may reduce the development and/or progression of symptoms associated with the pathological acetaminophen-induced toxicity.

Exemplary symptoms associated with acetaminophen-induced hepatotoxicity may include, but is not limited to, anorexia, nausea, vomiting, right upper quadrant abdominal pain, elevated AST, ALT, bilirubin and PT (INR), renal failure, pancreatitis, multiple organ failure. Mild acetaminophen poisoning may not cause symptoms, and when present, symptoms are usually minor until ≥48 h after ingestion. In some embodiments, the severity of symptoms of acetaminophen toxicity are quantified using 4 stages as shown in Table A.

TABLE A

Stages of acute acetaminophen poisoning

| Stage | Time Postingestion | Description |
|---|---|---|
| I | 0-24 h | Anorexia, nausea, vomiting |
| II | 24-72 h | Right upper quadrant abdominal pain (common) AST, ALT, and, if poisoning is severe, bilirubin and PT (INR) sometimes elevated |
| III | 72-96 h | Vomiting and symptoms of liver failure Peaking of AST, ALT, bilirubin and INR Sometimes renal failure and pancreatitis |
| IV | >5 days | Resolution of hepatotoxicity or progression to multiple organ failure (sometimes fatal) |

(b) Obtaining a Sample

A method of the disclosure comprises, in part, obtaining a biological sample from a subject. As used herein, the term "biological sample" refers to a sample obtained from a subject. Any biological sample comprising an acetaminophen-protein adduct is suitable. Numerous types of biological samples are known in the art. Suitable biological samples may include, but are not limited to, hair, tissue samples or bodily fluids. In some embodiments, the biological sample is a tissue sample such as a tissue biopsy. The tissue biopsy may be a biopsy of liver tissue. The biopsied tissue may be fixed, embedded in paraffin or plastic, and sectioned, or the biopsied tissue may be frozen and cryosectioned. Alternatively, the biopsied tissue may be processed into individual cells or an explant, or processed into a homogenate, a cell extract, a membranous fraction, or a protein extract. In other embodiments, the sample may be a bodily fluid. Non-limiting examples of suitable bodily fluids include blood, plasma, serum, urine, saliva, semen, perspiration, tears, mucus, sputum, tissue lystates or other excrement (e.g. feces). In a specific embodiment, the bodily fluid is urine. In another specific embodiment, the bodily fluid is plasma. In still another specific embodiment, the bodily fluid is serum. In yet still another specific embodiment, the bodily fluid is saliva. In a different embodiment, the biological sample is hair. The fluid may be used "as is", the cellular components may be isolated from the fluid, or a protein fraction may be isolated from the fluid using standard techniques.

As will be appreciated by a skilled artisan, the method of collecting a biological sample can and will vary depending upon the nature of the biological sample and the type of analysis to be performed. Any of a variety of methods generally known in the art may be utilized to collect a biological sample. Generally speaking, the method preferably maintains the integrity of the sample such that an acetaminophen-protein adduct can be accurately detected and the amount measured according to the invention.

A biological sample from a subject may be obtained by freshly collecting a sample, or may be obtained from a previously collected and stored sample. For instance, a biological sample may be obtained from a collection of stored and preserved blood samples. In some embodiments, a sample is obtained by freshly collecting a sample. In other embodiments, a sample is obtained from a previously collected and stored sample.

In some embodiments, a single sample is obtained from a subject to detect an APAP-protein adduct in the sample. Alternatively, an APAP-protein adduct may be detected in samples obtained over time from a subject. As such, more than one sample may be collected from a subject over time. For instance, 2, 3, 4, 5, 6, 7, 8, 9, 10, 11, 12, 13, 14, 15, 16 or more samples may be collected from a subject over time. In some embodiments, 2, 3, 4, 5, or 6 samples are collected from a subject over time. In other embodiments, 6, 7, 8, 9, or 10 samples are collected from a subject over time. In yet other embodiments, 10, 11, 12, 13, or 14 samples are collected from a subject over time. In other embodiments, 14, 15, 16 or more samples are collected from a subject over time.

When more than one sample is collected from a subject over time, samples may be collected every 0.5, 1, 2, 3, 4, 5, 6, 7, 8, 9, 10, 11, 12 or more hours. In some embodiments, samples are collected every 0.5, 1, 2, 3, or 4 hours. In other embodiments, samples are collected every 4, 5, 6, or 7 hours. In yet other embodiments, samples are collected every 7, 8, 9, or 10 hours. In other embodiments, samples are collected every 10, 11, 12 or more hours. Additionally, samples may be collected every 1, 2, 3, 4, 5, 6, 7, 8, 9, 10, 11, 12 or more days. In some embodiments, a sample is collected about every 6 days. In some embodiments, samples are collected every 1, 2, 3, 4, or 5 days. In other embodiments, samples are collected every 5, 6, 7, 8, or 9 days. In yet other embodiments, samples are collected every 9, 10, 11, 12 or more days.

(c) Detecting a Protein Adduct

A method of the disclosure comprises detecting one or more APAP-protein adducts in a sample from a subject. As used herein, the term "detecting an APAP-protein adduct" may be used to describe detecting the presence of an APAP-protein adduct, or detecting the presence and concentration or amount of an APAP-protein adduct in a sample from a subject. In specific embodiments, a method of the disclosure comprises detecting one or more APAP-protein adducts, wherein each APAP-protein adduct comprises a protein modified with NAPQI, and wherein the protein is selected from the group consisting of betaine-homocysteine S-methyltransferase 1, cytoplasmic aspartate aminotransferase, 1,4-alpha-glucan-branching enzyme, formimidoyltransferase-cyclodeaminase, or dystrophin.

In essence, an APAP-protein adduct may be detected using methods normally used in the art for detecting a specific protein in a sample. As such, non-limiting examples of methods of detecting a protein adduct may include chromatography, mass spectrometry, an antibody-based detection method, or a combination thereof, and may be as discussed in Ausubel et al. (2003) Current Protocols in Molecular Biology, John Wiley & Sons, New York, N.Y., or Sambrook et al. (1989) Molecular Cloning: A Laboratory Manual, Cold Spring Harbor Press, Cold Spring Harbor, N.Y.

In some embodiments, APAP-protein adducts of the disclosure are detected using mass spectrometry. Mass spectrometry may be tandem mass spectrometry, quadrupole mass spectrometry, MALDI-TOF mass spectrometry, inductively coupled plasma-mass spectrometry (ICP-MS), accelerator mass spectrometry (AMS), thermal ionization-mass spectrometry (TIMS), and spark source mass spectrometry (SSMS). In specific embodiments, APAP-protein adducts are detected using a mass spectrometry method capable of detecting a specific protein, and detecting a specific protein incremented by the molecular mass of NAPQI. Non-limiting examples of mass spectrometry methods capable of detecting a specific protein, and detecting a specific protein incremented by the molecular mass of NAPQI, include MALDI-TOF mass spectrometry and high-resolution tandem mass spectrometry. In an exemplary embodiment, MALDI-TOF mass spectrometry is used to detect APAP-protein adducts. In another exemplary embodiment, high-resolution tandem mass spectrometry is used to detect APAP-protein adducts.

In other embodiments, an APAP-protein adduct of the disclosure may be detected in a sample using methods based on epitope binding agents. Non-limiting examples of suitable epitope binding agents, depending upon the target molecule, include agents selected from the group consisting of an aptamer, an antibody, an antibody fragment, a double-stranded DNA sequence, modified nucleic acids, nucleic acid mimics, a ligand, a ligand fragment, a receptor, a receptor fragment, a polypeptide, a peptide, a coenzyme, a coregulator, an allosteric molecule, and an ion.

In some specific alternatives of the embodiments, an epitope binding agent is an antibody, and an APAP-protein adduct may be detected using antibody based methods. Non-limiting examples of antibodies that may be used include polyclonal antibodies, ascites, Fab fragments, Fab' fragments, monoclonal antibodies, single chain antibodies, humanized antibodies, and other fragments that contain the epitope binding site of the antibody.

Antibody based methods that may be used to detect a protein such as an APAP-protein adduct of the present disclosure are known in the art. Non-limiting examples of methods based on antibodies for detecting an APAP-protein adduct may include Western blotting, enzyme-linked immunosorbent assays (ELISA), or other solid phase immunoassays, a sandwich immunoassay, radioimmunoassay, nephelometry, electrophoresis, immunofluorescence, immunoblot, flow cytometry, immunohistochemistry, an array or other methods (see Ausubel, F. M. et al., eds., Current Protocols in Molecular Biology, John Wiley & Sons, including supplements through 2001).

In general, an antibody-based method of detecting and measuring an amount of an acetaminophen-protein adduct comprises contacting some or all of the sample comprising an acetaminophen-protein adduct with an anti-acetaminophen-protein adduct antibody under conditions effective to allow for formation of a complex between the antibody and the acetaminophen-protein adduct. Typically, the entire sample is not needed, allowing one skilled in the art to repeatedly detect and measure the amount of an acetaminophen-protein adduct in the sample over time. The method may occur in solution, or the antibody or acetaminophen-protein adduct may be immobilized on a solid surface. Non-limiting examples of suitable surfaces include microtitre plates, test tubes, beads, resins, and other polymers. Attachment to the substrate may occur in a wide variety of ways, as will be appreciated by those in the art. For example, the substrate and the antibody may be derivatized with chemical functional groups for subsequent attachment of the two. For example, the substrate may be derivatized with a chemical functional group including, but not limited to, amino groups, carboxyl groups, oxo groups or thiol groups. Using these functional groups, the antibody may be attached directly using the functional groups or indirectly using linkers. An anti-acetaminophen-protein adduct antibody may also be attached to the substrate non-covalently. For example, a biotinylated anti-acetaminophen-protein adduct antibody may be prepared, which may bind to surfaces covalently coated with streptavidin, resulting in attachment. Alternatively, an antibody may be synthesized on the surface using techniques such as photopolymerization and photolithography.

Contacting the sample with an antibody under effective conditions for a period of time sufficient to allow formation of a complex generally involves adding the anti-acetaminophen-protein adduct antibody composition to the sample and incubating the mixture for a period of time long enough for the anti-acetaminophen-protein adduct antibody to bind to any antigen present. After this time, the complex may be washed and then the complex is detected and the amount measured by any method well known in the art. Methods of detecting and measuring an amount of an antibody-polypeptide complex are generally based on the detection of a label or marker. The term "label", as used herein, refers to any substance attached to an antibody, or other substrate material, in which the substance is detectable by a detection method. Non-limiting examples of suitable labels include luminescent molecules, chemiluminescent molecules, fluorochromes, fluorescent quenching agents, colored molecules, radioisotopes, scintillants, biotin, avidin, stretpavidin, protein A, protein G, antibodies or fragments thereof, polyhistidine, $Ni^{2+}$, Flag tags, myc tags, heavy metals, and enzymes (including alkaline phosphatase, peroxidase, glucose oxidase and luciferase). Methods of detecting and measuring an amount of an antibody-polypeptide complex based on the detection of a label or marker are well known in the art.

In some embodiments, an antibody-based method is an immunoassay. Immunoassays can be run in a number of different formats. Generally speaking, immunoassays can be divided into two categories: competitive immmunoassays and non-competitive immunoassays. In a competitive immunoassay, an unlabeled analyte in a sample competes with labeled analyte to bind an antibody. Unbound analyte is washed away and the bound analyte is measured. In a non-competitive immunoassay, the antibody is labeled, not the analyte. Non-competitive immunoassays may use one antibody (e.g. the capture antibody is labeled) or more than one antibody (e.g. at least one capture antibody which is unlabeled and at least one "capping" or detection antibody which is labeled.) Suitable labels are described above.

In other embodiments, an antibody-based method is an immunoblot or Western blot. In yet other embodiments, an antibody-based method is flow cytometry. In different embodiments, an antibody-based method is immunohistochemistry (IHC). IHC uses an antibody to detect and quantify antigens in intact tissue samples. The tissue samples may be fresh-frozen and/or formalin-fixed, paraffin-embedded (or plastic-embedded) tissue blocks prepared for study by IHC. Methods of preparing tissue block for study by IHC, as well as methods of performing IHC are well known in the art.

In alternative embodiments, an antibody-based method is an array. An array comprises at least one address, wherein at least one address of the array has disposed thereon an anti-acetaminophen-protein adduct antibody. Arrays may comprise from about 1 to about several hundred thousand addresses. Several substrates suitable for the construction of arrays are known in the art, and one skilled in the art will appreciate that other substrates may become available as the art progresses. Suitable substrates are also described above. In some embodiments, the array comprises at least one anti-acetaminophen-protein adduct antibody attached to the substrate is located at one or more spatially defined addresses of the array. For example, an array may comprise at least one, at least two, at least three, at least four, or at least five anti-acetaminophen-protein adduct antibodies, each antibody recognizing the same or different acetaminophen-protein adducts, and each antibody may be may be at one, two, three, four, five, six, seven, eight, nine, ten or more spatially defined addresses.

An antibody based method that may be used to detect an APAP-protein adduct comprises using any antibody with specificity for NAPQI bound to a protein. Non-limiting examples of an antibody with specificity for APAP bound to a protein include antibodies that recognize the acetaminophen-cysteine adducts. Such antibodies are known in the art and may be as described in Bartolone et al. (1987; Biochem Pharmacol. 36:1193-1196), Roberts et al. (1987 J Pharmacol Exp Ther. 241:527-533), Bartolone et al. (1988 Biochem. Pharmacol. 37:4763-4774), Pumford et al. (1989, J Pharmacol Exp Ther 248: 190-196), and Pumford et al. (1990, Toxicol Appl Pharmacol 104:521-532), the disclosures of which are incorporated herein in their entirety.

An antibody with specificity for NAPQI bound to a protein may be specific for any epitope associated with NAPQI bound to a protein. In some embodiments, an antibody with specificity for NAPQI bound to a protein may be specific for the parent drug acetaminophen but also recognize acetaminophen bound to protein. In other embodiments, an antibody with specificity for NAPQI bound to a protein may be specific for free NAPQI but also recognize NAPQI bound to protein. In specific embodiments, an antibody with specificity for NAPQI bound to a protein may be specific for NAPQI covalently bound to protein. For instance, an antibody with specificity for NAPQI bound to a protein may be specific for a 3-(cystein-S-yl) APAP (3-Cys-A)-protein linkage, or may be specific for an APAP-protein linkage at carbon 4 of the APAP ring via a —S-linkage. In an exemplary embodiment, an antibody with specificity for NAPQI bound to a protein is specific for NAPQI bound to a protein through a 3-(cystein-S-yl) APAP (3-Cys-A)-protein linkage.

For each of the foregoing embodiments, a protein that may be modified by NAPQI may be first isolated or enriched before detection. For instance, proteins that may be modified by NAPQI may be enriched or isolated using liquid chromatography, by precipitation, electrophoresis, or affinity purification. In some embodiments, proteins are enriched or purified using liquid chromatography. In other embodiments, proteins that may be modified by NAPQI are enriched or purified using electrophoresis.

In specific embodiments, proteins are enriched or purified by affinity purification before detection. In particularly specific embodiments, proteins are enriched or purified by affinity purification using antibodies with specificity to a protein that may be modified by NAPQI. Methods of enriching a sample for a protein or purifying a protein using affinity purification are known in the art. In short, affinity purification comprises incubating a sample with a solid support, such as beads, a culture plate, or a membrane, that facilitates later steps. A solid support may be coated with antibodies specific to proteins that may be modified by NAPQI, causing proteins that may be modified by NAPQI to attach to the solid support. Alternatively, a sample may be incubated with a first antibody with specificity to a protein that may be modified by NAPQI, and the NAPQI-protein-antibody complex may be isolated by incubating with a solid support coated with a second antibody with specificity against a second site on said first antibody, causing a protein-antibody complex to attach to the solid support. Acetaminophen-protein adducts may then be purified or enriched by washing other material in the sample that is not bound to the solid support, or, if the solid support is superparamagnetic beads, proteins that may be modified by NAPQI attached to the beads (expressing the antigen) may be separated from the sample by attraction to a strong magnetic field. Upon enrichment or purification of a protein, an APAP-adducted protein may then be detected in the enriched or purified sample using any of the methods described above.

In some exemplary embodiments, a method of the disclosure comprises using protein-specific antibodies to capture and isolate one or more proteins that may be modified with NAPQI, and then using a second immunoassay with specificity for NAPQI bound to a protein to detect the APAP-protein adducts. In other exemplary embodiments, a method of the disclosure comprises using NAPQI-specific antibodies to capture and isolate one or more proteins that may be modified with NAPQI, and then using a second immunoassay with specificity for a protein that may be modified with NAPQI to detect the APAP-protein adducts.

The disclosure also provides that multiple APAP-protein adducts in the same biological sample may be measured simultaneously. Additionally, the disclosure provides that APAP-protein adducts and corresponding non-adducted proteins may be detected in the same biological sample. As such, the disclosure provides a useful method for screening changes in synthesis and clearance of APAP-adducted proteins on a large scale (i.e., proteomics/metabolomics) and provides a sensitive means to detect and measure APAP-adducted proteins.

In some embodiments, total APAP-protein adducts in a sample from a subject may also be detected. Methods of detecting total APAP-protein adducts in a sample are known in the art. In some embodiments, total APAP-protein adducts in a sample are detected using liquid chromatography. Liquid chromatography may be high performance liquid chromatography (HPLC). Non-limiting examples of HPLC may include partition chromatography, normal phase chromatography, displacement chromatography, reverse phase chromatography, size exclusion chromatography, ion exchange chromatography, bioaffinity chromatography, or aqueous normal phase chromatography. Non-limiting detection methods that may be used in conjunction with HPLC to detect total APAP-protein adducts include electrochemical detection, detection using ultraviolet or visible spectroscopy, fluorescence, a chiral detector, a photodiode array, or detection methods based on mass spectrometry. In a specific alternative of the embodiments, total APAP-protein adducts in a sample are detected using HPLC with electrochemical detection (HPLC-ECD). In an exemplary embodiment, total APAP-protein adducts are detected using HPLC-ECD as described in Muldrew et al., 2002, Drug Metabolism and Disposition 30:446-451, the disclosure of which is incorporated herein in its entirety.

(d) Detecting Acetaminophen-Induced Toxicity in a Subject

In aspect, the invention provides means to classify a subject based on the amount of acetaminophen-protein adduct measured in a biological sample obtained from the subject. The method generally comprises (i) obtaining a biological sample from a subject and measuring the amount of acetaminophen-protein adduct in the sample, (ii) comparing the amount of acetaminophen-protein adduct in the sample to a reference value, and (iii) classifying the subject as having a high or low amount of acetaminophen-protein adduct based on the amount of acetaminophen-protein adduct measured in the sample. In the foregoing methodology, one or more acetaminophen protein adducts may be measured. For example, 1, 2, 3, 4, 5, 6, 7, 8, 9 or 10 acetaminophen protein adducts may be measured. Methods for obtaining a biological sample from a subject and measuring the amount of acetaminophen-protein adduct in the sample are detailed above. In a preferred embodiment, the biological sample is biological fluid selected from the group consisting of blood, plasma, serum, urine and saliva.

In some embodiments, acetaminophen-protein adducts comprise a protein modified with NAPQI, wherein the protein modified with NAPQI is selected from the group consisting of betaine-homocysteine S-methyltransferase 1, cytoplasmic aspartate aminotransferase, 1,4-alpha-glucan-branching enzyme, formimidoyltransferase-cyclodeaminase, or dystrophin. In one embodiment, betaine-homocysteine S-methyltransferase 1 modified with NAPQI is detected. In another embodiment, cytoplasmic aspartate aminotransferase modified with NAPQI is detected. In another embodiment, 1,4-alpha-glucan-branching enzyme modified with NAPQI is detected. In an additional embodiment, formimidoyltransferase-cyclodeaminase modified with NAPQI is detected. In yet another embodiment, dystrophin modified with NAPQI is detected.

In other embodiments, more than one APAP-protein adduct is detected, wherein each APAP-protein adduct comprises a protein modified with NAPQI, and wherein the protein is selected from the group consisting of betaine-homocysteine S-methyltransferase 1, cytoplasmic aspartate aminotransferase, 1,4-alpha-glucan-branching enzyme, formimidoyltransferase-cyclodeaminase, or dystrophin. For instance, two, three, four, or five APAP-protein adducts are detected, wherein each APAP-protein adduct comprises a protein modified with NAPQI, and wherein the protein is selected from the group consisting of betaine-homocysteine S-methyltransferase 1, cytoplasmic aspartate aminotransferase, 1,4-alpha-glucan-branching enzyme, formimidoyltransferase-cyclodeaminase, or dystrophin. In one embodiment, two APAP-protein adducts are detected. In another embodiment, three APAP-protein adducts are detected. In yet another embodiment, four APAP-protein adducts are detected. In another embodiment, five APAP-protein adducts are detected.

In some embodiments, one or more APAP-protein adducts are detected, wherein the APAP-protein adduct comprises a protein modified with NAPQI, and wherein the one or more proteins modified with NAPQI are as described in Table B.

TABLE B

BHMT
cAspAT
1,4-alpha-glucan-branching enzyme
FTCD
dystrophin
BHMT, cAspAT
BHMT, 1,4-alpha-glucan-branching enzyme
BHMT, FTCD
BHMT, dystrophin
cAspAT, 1,4-alpha-glucan-branching enzyme
cAspAT, FTCD
cAspAT, dystrophin TABLE B-continued 1,4-alpha-glucan-branching enzyme, FTCD
1,4-alpha-glucan-branching enzyme, dystrophin
FTCD, dystrophin
BHMT, cAspAT, 1,4-alpha-glucan-branching enzyme
BHMT, cAspAT, FTCD
BHMT, cAspAT, dystrophin
BHMT, 1,4-alpha-glucan-branching enzyme, FTCD
BHMT, 1,4-alpha-glucan-branching enzyme, dystrophin
BHMT, FTCD, dystrophin
cAspAT, 1,4-alpha-glucan-branching enzyme, FTCD
cAspAT, 1,4-alpha-glucan-branching enzyme, dystrophin
cAspAT, FTCD, dystrophin
1,4-alpha-glucan-branching enzyme, FTCD, dystrophin
BHMT, cAspAT, 1,4-alpha-glucan-branching enzyme, FTCD
BHMT, cAspAT, 1,4-alpha-glucan-branching enzyme, dystrophin
BHMT, cAspAT, FTCD, dystrophin
BHMT, 1,4-alpha-glucan-branching enzyme, FTCD, dystrophin
cAspAT, 1,4-alpha-glucan-branching enzyme, FTCD, dystrophin
BHMT, cAspAT, 1,4-alpha-glucan-branching enzyme, FTCD, dystrophin The amount of acetaminophen-protein adduct in the sample is compared to a reference value. Any suitable reference value known in the art may be used. For example, a suitable reference value may be the amount of acetaminophen-protein adduct in a biological fluid sample obtained from a subject or group of subjects of the same species that has normal hepatic function. In another example, a suitable reference value may be the amount of acetaminophen-protein adduct in a biological fluid sample obtained from a subject, or group of subjects, of the same species that has no detectable acetaminophen-induced toxicity. In another example, a suitable reference value may be the amount of acetaminophen-protein adduct in biological fluid sample obtained from a subject or group of subjects of the same species that has acetaminophen-induced toxicity as measured by AST, ALT, bilirubin, INR or other non-specific biomarkers of hepatic function. For example, a suitable reference value may be the amount of acetaminophen-protein adduct in a biological sample obtained from a subject or group of subjects of the same species that has acetaminophen-induced toxicity as measured by ALT levels >1000 IU. In another example, a suitable reference value may be the background signal of the assay as determined by methods known in the art. In another example, a suitable reference value may be a measurement of the amount of acetaminophen-protein adduct in a reference sample obtained from the same subject. The reference sample comprises the same type of biological fluid as the test sample, and may or may not be obtained from the subject when hepatic function was normal. A skilled artisan will appreciate that it is not always possible or desirable to obtain a reference sample from a subject when the subject is otherwise healthy. For example, in an acute setting, a reference sample may be the first sample obtained from the subject at presentation. In another example, when monitoring the effectiveness of a therapy, a reference sample may be a sample obtained from a subject before therapy began. In such an example, a subject may have suspected acetaminophen-induced toxicity but may not have other symptoms of acetaminophen-induced toxicity or the subject may have suspected acetaminophen-induced toxicity and one or more other symptom of acetaminophen-induced toxicity. In a specific embodiment, a suitable reference value may be a threshold previously determined via other methods. For example, a suitable reference value may be a value corresponding to 1 nmol/ml of acetaminophen-protein adduct as measured by high pressure liquid chromatography with electrochemical detection (HPLC-EC). It should be appreciated by those of skill in the art that in such embodiments, a reference value of the one or more APAP-protein adducts may be determined for each APAP-protein adduct.

According to the invention, a subject may be classified based on the amount of acetaminophen-protein adduct measured in the sample. Classifying a subject based on the amount of acetaminophen-protein adduct measured in a sample of biological fluid obtained from the subject may be used to identify subjects with acetaminophen-induced toxicity. The term "acetaminophen-induced toxicity" is described in detail below. Generally speaking, a subject may be classified as having a high or low amount of acetaminophen-protein adduct compared to a reference value, wherein a high amount of acetaminophen-protein adduct is an amount above the reference value and a low amount is an amount equal to or below the reference value. In preferred embodiments, to classify a subject as having a high amount of acetaminophen-protein adduct, the amount of acetaminophen-protein adduct in the sample compared to the reference value may be at least 5% greater. For example, the amount of acetaminophen-protein adduct in the sample may be at least 5%, at least 10%, at least 20%, at least 30%, at least 40%, at least 50%, at least 60%, at least 70%, at least 80%, at least 90%, or at least 100% greater than the reference value. In other embodiments, the amount of acetaminophen-protein adduct in the sample of biological fluid obtained from the subject compared to the reference value may be increased by greater than 1-fold. For example, the amount of acetaminophen-protein adduct in the sample compared to the reference value may be increased at least 1.5-fold, at least 2-fold, at least 2.5-fold, at least 3-fold, at least 3.5-fold, at least 4-fold, at least 4.5 fold, or at least 5-fold. Alternatively, the amount of acetaminophen-protein adduct in the sample compared to the reference value may be increased by at least 5.5-fold, at least 6-fold, at least 6.5-fold, at least 7-fold, at least 7.5-fold, at least 8-fold, at least 8.5-fold, at least 9-fold, at least 9.5 fold, at least 10-fold, at least 15-fold, at least 20-fold, at least 25-fold, at least 30-fold, at least 35-fold, at least 40-fold, at least 45-fold, or at least 50-fold.

In another aspect, the invention provides means to detect acetaminophen-induced toxicity in a subject. As used herein, the term "acetaminophen-induced toxicity" refers to damage or destruction to the liver due to acetaminophen. Acetaminophen, when taken in overdoses and sometimes even when introduced within therapeutic ranges, may injure the liver. Damage to the liver is not due to the drug itself but to a toxic metabolite (N-acetyl-p-benzoquinone imine NAPQI, or NABQI) produced by cytochrome P-450 enzymes in the liver. In an overdose, a large amount of NAPQI is generated, which overwhelms the detoxification process and leads to liver cell damage. The risk of liver injury is influenced by several factors including the dose ingested, concurrent alcohol or other drug intake, interval between ingestion and antidote, etc. The dose toxic to the liver is quite variable from person to person and is smaller in chronic alcoholics. The causes of hepatoxicity known in the art are numerous, and may include, but are not limited to, trauma, neoplastic disease, bacterial or viral infection, exposure to toxins, poisons, environmental, or other substances. Biomarkers of liver function are well known in the art. Non-limiting examples of biomarkers of liver injury include elevated AST, ALT, bilirubin and PT (INR). However, increased acetaminophen-protein adduct in a biological fluid may prove that acetaminophen caused or contributed to the liver injury.

In some embodiments, acetaminophen-induced toxicity is detected when the concentration of one or more APAP-protein adducts detected in a sample from a subject is above the reference value. For instance, acetaminophen-induced toxicity is diagnosed when the concentration of 1, 2, 3, 4, or 5 of the APAP-protein adducts of the disclosure detected in a sample is above the reference value. In one embodiment, acetaminophen-induced toxicity is detected when the concentration of one APAP-protein adduct detected in a sample is above the reference value. In another embodiment, acetaminophen-induced toxicity is detected when the concentrations of two APAP-protein adducts detected in a sample are above the reference value. In yet another embodiment, acetaminophen-induced toxicity is detected when the concentrations of three APAP-protein adducts detected in a sample are above the reference value. In another embodiment, acetaminophen-induced toxicity is detected when the concentrations of four APAP-protein adducts detected in a sample are above the reference value. In an additional embodiment, acetaminophen-induced toxicity is detected when the concentrations of five APAP-protein adducts detected in a sample are above the reference value. In some embodiments, acetaminophen-induced toxicity is detected when the concentration of an APAP-protein adduct is above the reference value, wherein each APAP-protein adduct comprises a protein modified with NAPQI, and wherein the protein is as described in Table B.

In addition to the detection of acetaminophen-induced toxicity, it should also be appreciated by those of skill in the art that a method of the disclosure may be used to diagnose various features of treatment with acetaminophen and acetaminophen toxicity. A method of the disclosure may be used to determine levels of acetaminophen intake by a subject to determine compliance with treatment. Alternatively, a method of the disclosure may be used to determine the severity of acetaminophen toxicity. For instance, a method of the disclosure may be used to determine normal sub-toxic levels of acetaminophen, thereby ruling out acetaminophen toxicity. A method of the disclosure may also be used to diagnose acetaminophen toxicity with good prognosis that will resolve. Alternatively, a method of the disclosure may be used to diagnose acetaminophen toxicity with bad prognosis that will lead to death or the need for a liver transplant. A method of the disclosure may also be used to determine chronic acetaminophen exposure. As used herein, the term "chronic acetaminophen exposure" may be used to describe acetaminophen toxicity caused by exposure to repeated supratherapeutic acetaminophen over extended periods of time, such as, for instance, through ingesting supratherapeutic doses of acetaminophen, or use of sustained release acetaminophen formulations. Additionally, a method of the disclosure may be used to determine acute acetaminophen exposure. As used herein, the term "acute acetaminophen exposure" may be used to describe acetaminophen toxicity caused by ingestion of a single large dose of acetaminophen.

A method of the present disclosure may be used in combination with other methods of diagnosing acetaminophen toxicity, or other clinical diagnostic methods.

Upon detection of diagnosis of acetaminophen-induced toxicity, the subject may be treated via methods standard in the art for acetaminophen-induced toxicity. Such treatment methods may depend on the severity of the acetaminophen-induced toxicity. Treatment of acetaminophen overdose consists primarily of GI decontamination and supportive care. The subject may be administered activated charcoal, N-acetylcysteine (NAC), or in severe cases, liver transplantation may need to occur.

For each aspect, the method generally comprises (i) obtaining a biological sample from a subject, (ii) measuring the amount of acetaminophen-protein adduct in the sample, and (iii) comparing the amount of acetaminophen-protein adduct in the sample to a reference value. A greater amount of acetaminophen-protein adduct in the sample compared to the reference value indicates acetaminophen-induced toxicity. The amount of acetaminophen-protein adduct may be a qualitative, a semi-quantitative or quantitative measurement. Suitable acetaminophen-protein adducts are described above, as are methods for measuring the amount of acetaminophen-protein adduct in a biological sample. In a preferred embodiment, the biological sample is biological fluid selected from the group consisting of blood, plasma, serum, urine and saliva.

Methods of the present disclosure may also be used to determine a profile of APAP-protein adducts in a sample from a subject. As used herein, a "profile of APAP-protein adducts" may be used to describe the identity and/or the concentration of one or more APAP-protein adducts in a sample from a subject, or the fluctuation of the identity and/or concentration of APAP-protein adducts over time in samples from a subject. In some embodiments, a profile of APAP-protein adducts may comprise one or more APAP-protein adducts, wherein each of the one or more APAP-protein adducts comprises a protein modified with NAPQI, and wherein the protein is as described in Table B.

As such, a method of the disclosure may comprise comparing a profile of APAP-protein adducts in a sample from a subject to a database comprising the identity and concentration of one or more APAP-protein adducts correlated with APAP toxicity, identifying a matching entry of the database in which the identity and concentration of the one or more APAP-protein adducts matches the identity and concentration of the profile of the at least one APAP-protein adduct in the sample, and determining the acetaminophen toxicity comprising the particular acetaminophen toxicity of the matching entry.

Definitions

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

In practicing the present disclosure, many conventional techniques in molecular biology, microbiology, and recombinant DNA may be used. These techniques are well known and are explained in, for example, Current Protocols in Molecular Biology, Volumes I, II, and III, 1997 (F. M. Ausubel ed.); Sambrook et al., 1989, Molecular Cloning: A Laboratory Manual, Second Edition, Cold Spring Harbor Laboratory Press, Cold Spring Harbor, N.Y.; DNA Cloning: A Practical Approach, Volumes I and II, 1985 (D. N. Glover ed.); Oligonucleotide Synthesis, 1984 (M. L. Gait ed.); Nucleic Acid Hybridization, 1985 (Hames and Higgins eds.); Transcription and Translation, 1984 (Hames and Higgins eds.); Animal Cell Culture, 1986 (R. I. Freshney ed.); Immobilized Cells and Enzymes, 1986 (IRL Press); Perbal, 1984, A Practical Guide to Molecular Cloning; the series, Methods in Enzymology (Academic Press, Inc.); Gene Transfer Vectors for Mammalian cells, 1987 (J. H. Miller and M. P. Calos eds., Cold Spring Harbor Laboratory); and Methods in Enzymology, Vol. 154 and Vol. 155 (Wu and Grossman, and Wu, eds., respectively).

The terms "APAP adduct" or "APAP-protein adduct" may be used interchangeably to describe a protein modified with NAPQI, and wherein the protein is selected from the group consisting of betaine-homocysteine S-methyltransferase 1, cytoplasmic aspartate aminotransferase, 1,4-alpha-glucan-branching enzyme, formimidoyltransferase-cyclodeaminase, or dystrophin.

The term "supratherapeutic dose of APAP" or "toxic dose of APAP" may be used interchangeably to describe an excessive dose of APAP that may cause toxicity (e.g., liver damage) in a subject.

EXAMPLES

The following examples are included to demonstrate preferred embodiments of the disclosure. It should be appreciated by those of skill in the art that the techniques disclosed in the examples that follow represent techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1. Identification of Proteins Modified by NAPQI in Serum from Patients with Significant Acetaminophen Toxicity Acetaminophen (APAP) is the most common drug used for the treatment of pain and fever in the world today and is also the leading cause of acute liver failure in the United States. The initial stages of APAP toxicity have been well-characterized and involve the biotransformation of the parent drug to a chemically reactive metabolite N-acetyl-p-benzoquinone imine (NAPQI), which binds covalently to cellular proteins. NAPQI is detoxified by binding to the cysteinyl thiol on hepatic glutathione (GSH). In toxic APAP exposures, GSH reserves are depleted, increasing the amount of NAPQI that binds to cysteinyl thiols on cellular proteins, producing a variety of APAP-protein adducts. Toxicity occurs with lysis of hepatocytes and release of the modified proteins into the serum. Proteins that are modified in humans by NAPQI have not been previously reported.

In this example, the identification of specific acetaminophen-adducted proteins in serum from acetaminophen overdose patients is reported. State-of-the-art, adduct-focused proteomic approaches were used to identify specific "second generation" biomarkers of APAP toxicity in patients receiving therapeutic doses of APAP and patients that have received overdoses of APAP. Identification of specific APAP-protein adducts and examination of these specific adducts relative to newly described metabolomic markers of APAP toxicity and established indices of liver toxicity may lay the foundation for improved future assessments of risk and safety for APAP in patients.

Proteomic studies based on tandem mass spectrometry (MS/MS) were used to unambiguously determine proteins modified by NAPQI (adducted proteins) in serum from patients with significant acetaminophen toxicity. These proteins are shown in Table 1. Table 1 also shows at least one cysteine site modification on each protein.

TABLE 1

| Protein name | Molecular weight (KDa) | Protein ID; Cystein modified |
|---|---|---|
| Betaine-homocysteine S-methyltransferase 1 | 45 | Q93088; Cys131 |

TABLE 1-continued

| Protein name | Molecular weight (KDa) | Protein ID; Cystein modified |
|---|---|---|
| Aspartate aminotransferase, cytoplasmic | 46 | P17174; Cys46 |
| 1,4-alpha-glucan-branching enzyme | 80 | Q04446; Cys81 |
| Formimidoyltransferase-cyclodeaminase | 59 | O95954; Cys131 |
| Dystrophin | 427 | P11532; Cys1040 |

Proteins modified with acetaminophen did not occur in control serum from individuals that were not exposed to acetaminophen.

Example 2. Detection of NAPQI Adducted Proteins

To test whether specific NAPQI modified proteins, such as the proteins described in Example 1, may be specifically detected, ovalbumin (OA) and bovine serum albumin (BSA) proteins were reacted with synthetically prepared NAPQI, and submitted for proteomics evaluation using MS/MS. The MS/MS proteomic analysis was capable of determining the molecular mass of the protein incremented by the molecular mass of NAPQI (149), and the specific site(s) of modification were determined. The MS/MS proteomic analysis was also capable of determining the molecular mass of the protein incremented by the molecular mass of more than one NAPQI (149n, wherein n is the number of NAPQI adducted to the protein). In addition, the specifically modified adduct proteins (OA-APAP and BSA-APAP) were recognized by an anti-adduct antibody developed by the inventors, and could thus be quantitated by immunoassay.

Example 3. Development of Immunoassay for Acetaminophen Toxicity

The identification of NAPQI adducted proteins described in Example 1 may allow development of a specific immunoassay for acetaminophen toxicity. The disclosure may be based on the use of protein-specific antibodies to capture and isolate adducted protein(s), and then utilization of a second immunoassay specific for acetaminophen-cysteine adducts (total adducts) to detect the adduction of the protein.

Human acetaminophen overdose and exposure samples may be analyzed to understand the frequency of occurrence of the specific protein adducts among different degrees of severity of toxicity. To accomplish this, additional methodology may be developed to antibody/affinity isolate adduct proteins and thus enrich for the specific proteins from human samples. For example, assays using solid-phase antibodies to specific protein (on paramagnetic beads or other solid phase matrix) to capture the specific protein may be performed and complimented with detection of adduct proteins using antibodies with specificity for APAP bound to protein via the physiologically formed linkage from C3 of acetaminophen to S of cysteine residues. Essentially the assay may involve interrogating the adducted protein two times: 1) capture by specific anti-protein antibody, and 2) detection with antibodies specific for the hapten protein linkage. Commercially available anti-protein antibodies, or newly-developed antibodies designed specifically for the use described herein, may be used. Alternatively, the assay may involve interrogating the adducted protein by capturing with antibodies specific for the hapten protein linkage, and detecting with antibodies specific for the protein.

What is claimed is:

1. A method of treating acetaminophen-induced toxicity in a subject in need thereof, the method comprising:
    a) obtaining a biological sample from the subject;
    b) measuring the amount of acetaminophen (APAP)-protein adduct in the sample by detecting one or more APAP-protein adducts, wherein each APAP-protein adduct comprises a protein covalently modified with N-acetyl-p-benzoquinone (NAPQI), and wherein the protein is selected from the group consisting of betaine-homocysteine S-methyltransferase 1, cytoplasmic aspartate aminotransferase, 1,4-alpha-glucan-branching enzyme, formimidoyltransferase-cyclodeaminase, and dystrophin;
    c) comparing the measured amount of the acetaminophen-protein adduct in the sample to a reference value, wherein a greater amount of acetaminophen-protein adduct in the sample compared to the reference value indicates acetaminophen-induced toxicity in the subject; and
    d) administering treatment for acetaminophen-induced toxicity after step c) to the subject.

2. The method of claim 1, wherein the acetaminophen-induced toxicity is directly or indirectly associated with acetaminophen overdose.

3. The method of claim 1, wherein the acetaminophen-induced toxicity is hepatotoxicity.

4. The method of claim 1, wherein the biological sample is a biological fluid selected from the group consisting of blood, plasma, serum, urine, saliva and hair.

5. The method of claim 1, wherein the biological sample is from a subject with hepatotoxicity of unknown etiology.

6. A method of treating acetaminophen-induced toxicity in a subject in need thereof, the method comprising:
    a) obtaining a sample from the subject;
    b) measuring the amount of acetaminophen (APAP)-protein adduct in the sample to determine a profile of APAP-protein adducts in the subject, the profile comprising the identity and concentration in the sample from the subject of one or more APAP-protein adducts, wherein each APAP-protein adduct comprises a protein covalently modified with N-acetyl-p-benzoquinone (NAPQI), and wherein the protein is selected from the group consisting of betaine-homocysteine S-methyltransferase 1, cytoplasmic aspartate aminotransferase, 1,4-alpha-glucan-branching enzyme, formimidoyltransferase-cyclodeaminase, and dystrophin;
    c) comparing the profile determined in (b) to a database comprising the presence and concentration of one or more APAP-protein adducts correlated with acetaminophen toxicity;
    d) identifying a matching entry of the database in which the identity and concentration of the one or more APAP-protein adducts matches the identity and concentration of the one or more APAP-protein adducts in the sample;
    e) determining the acetaminophen toxicity comprising the particular acetaminophen toxicity of the matching entry; and
    f) administering treatment for acetaminophen-induced toxicity after step e) to the subject.

* * * * *